United States Patent [19]

Kvavle et al.

[11] 4,007,732
[45] Feb. 15, 1977

[54] METHOD FOR LOCATION AND REMOVAL OF SOFT TISSUE IN HUMAN BIOPSY OPERATIONS

[76] Inventors: Robert Carl Kvavle, Rte. 2 Box 157A, Hillsboro, Oreg. 97123; William Chester Awe, 15035 NW. Perimeter Drive, Beaverton, Oreg. 97005

[22] Filed: Sept. 2, 1975

[21] Appl. No.: 609,296

[52] U.S. Cl. ............................... 128/2 B; 128/2 A; 250/312
[51] Int. Cl.² ......................................... A61B 10/00
[58] Field of Search ....... 128/2 A, 2 B, 418, 419 P; 250/312, 476

[56] References Cited

UNITED STATES PATENTS

| | | | |
|---|---|---|---|
| 1,275,669 | 8/1918 | Forbes | 250/312 |
| 3,087,486 | 4/1963 | Kilpatrick | 128/418 X |
| 3,516,412 | 6/1970 | Ackerman | 128/419 P X |
| 3,547,121 | 12/1970 | Cherry | 250/476 X |
| 3,836,776 | 9/1974 | Gullekson | 250/312 |
| 3,902,501 | 9/1975 | Citron et al. | 128/419 P X |

OTHER PUBLICATIONS

Portsmann, W., et al., Amer. Journ. of Cardiology, vol. 30, July 11, 1972, pp. 74–75.

*Primary Examiner*—Kyle L. Howell

[57] ABSTRACT

X-ray techniques are used to detect early evidence of breast cancer. When such evidence is found, a target is implanted in the suspect area while the patient is being x-rayed. The target has an attached line which leads from the target out through the skin of the patient. A biopsy is made with a cutting tool guided on the line attached to the target, thereby obtaining a biopsy specimen accurately centered on the suspect area.

2 Claims, 6 Drawing Figures

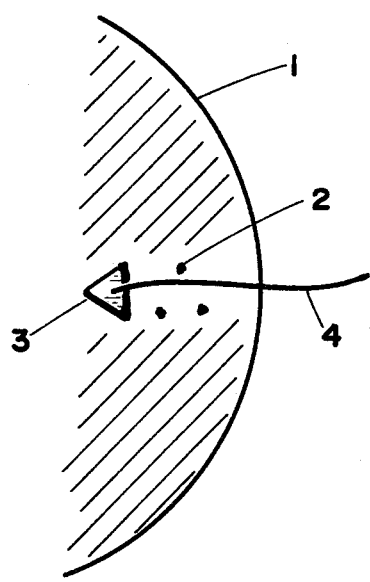
Fig_1_
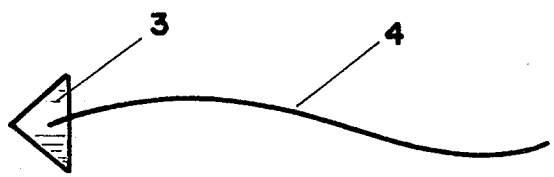
Fig_2_
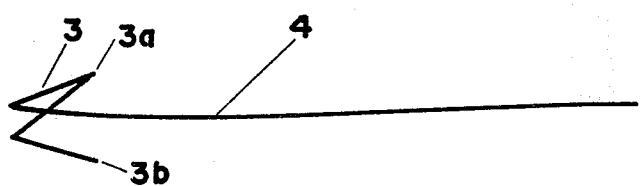
Fig_3_

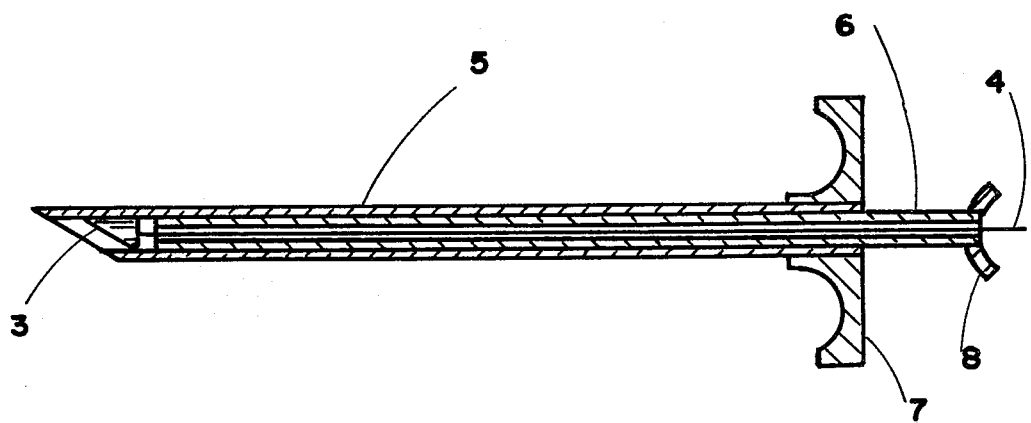
Fig_4_

METHOD FOR LOCATION AND REMOVAL OF SOFT TISSUE IN HUMAN BIOPSY OPERATIONS

BACKGROUND OF THE INVENTION

The present invention consists of a method to accurately locate and to precisely remove soft tissue specimens in human biopsy operations.

In the diagnosis and treatment of tumors and particularly in the treatment of breast cancer in females, it is of great importance to locate and treat malignancies at their earliest stage of growth. Such early tumors are detected by the presence of minute, x-ray opaque deposits known as microcalcifications. In the present state of the art women are encouraged to routinely submit themselves for examination by radiography techniques. These examinations detect the minute deposits which can indicate the presence of early cancer. In the event that such deposits are found, a biopsy is advised to determine if cancer actually exists. About one in ten of these biopsies are positive.

The major technical problem in biopsy is difficulty in locating the area in the breast shown on the x-ray because the lesions are usually small and cannot be felt by the surgeon. Attempts have been made to mark the location of observed deposits on a chart or to inject a dye into the area containing the lesions. The dye, however, tends to diffuse into adjacent tissue in a short time and is, therefore, of limited value.

In consequence of the limited and inaccurate means of marking the suspected tumor location and, additionally, because of the dimensionally unstable character of breast tissue, a surgeon will remove substantial quantities of breast tissue to insure that he obtains the area of suspected malignancy. Even then, subsequent examination of the removed tissue may reveal the biopsy was not well located and a second biopsy may be required. Such biopsy procedures result in undue physical deformity and increase surgical morbidity.

SUMMARY OF THE INVENTION

The present invention provides a unique method to accurately locate and precisely remove the area of suspected malignancy thereby reducing the size of specimen taken.

A primary feature of the invention is the marking of the lesion with an x-ray opaque, fixed marker or target which can be inserted in deep tissue with a needle.

Another feature of the invention is that positive location of the target is maintained by use of an attached fine steel wire or similar means which is caused to extend out and through the skin for locating and guiding purposes.

Another feature of the invention is that a cutting device is guided on the wire so as to accurately center itself about the implanted target as the biopsy is made, thus obtaining a biopsy specimen which contains the marked lesion at its center.

Further objects, features, and advantages of the present invention will be apparent from the following detailed description which is referred to the accompanying drawings:

BRIEF DESCRIPTION OF THE DRAWINGS

In the drawings:

FIG. 1 is a simplified section of a human breast showing lesions and an implanted target and guide wire.

FIG. 2 is a plan view of a target with an attached wire.

FIG. 3 is a plan view of a target formed from wire as an alternate construction to that in FIG. 2.

FIG. 4 is an enlarged sectional view of a needle mechanism containing a target for insertion in deep tissue.

DETAILED DESCRIPTION OF THE PREFERRED EMBODIMENTS

Figure 5:
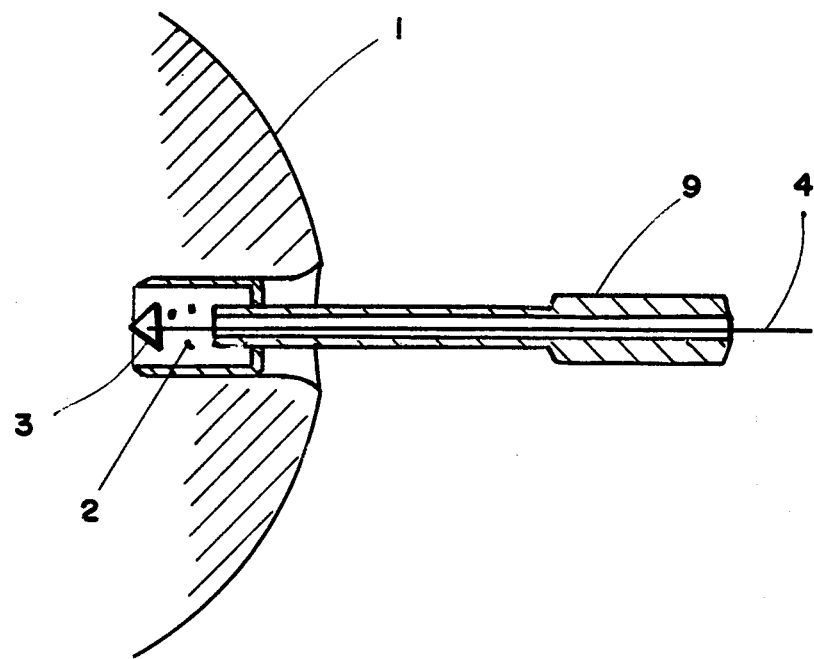
FIG. 5 is a sectional view of a human breast showing the lesions, the implanted target and guide wire and the cutting tool in position as a biopsy is made.

A simplified cross section of a human breast 1 is given in FIG. 1 in which minute lesions 2 visible to x-ray examination are shown. When such deposits are observed a target 3 is implanted and securely anchored in the immediate area.

Attached to target 3 and extending outwardly and externally to breast 1 is wire 4 which serves as the means to locate target 3 when the biopsy is made. The biopsy may be made at another time and place; therefore, the exposed portion of wire 4 may be coiled flat against the skin under a sterile dressing for the interim period.

The target 3 and attached locating means 4 are shown in FIG. 2 and FIG. 3 as optional embodiments of the invention.

In FIG. 2 the target is made from flat, thin, resilient material such as stainless steel sheet metal, and the wire is attached by welding.

In FIG. 3 the target 3 is formed by bending the end of wire 4 to form one or more barbs 3a, 3b. In both configurations, the targets are resilient so that they may be compressed and loaded into an implanting device.

The target is implanted in the breast by means of a hollow needle mechanism shown in FIG. 4. This mechanism consists of a hollow needle 5 sharpened on one end and fitted with a cooperating plunger 6, which plunger is also hollow so that locating wire 4 may pass through and be contained therein. Target 3 is mounted in a compressed condition within and near the end of hollow needle 5 in such a manner that a small movement of plunger 6 is sufficient to dislodge target 3 from said needle whereupon said target immediately expands and anchors itself in the surrounding tissue.

As the needle mechanism of FIG. 4 is withdrawn from the breast after making the implant, wire 4 is pulled from said needle mechanism by the anchored target 3 to which it is attached. By this method and means wire 4 is caused to extend from implanted target 3 along the path of the needle withdrawal outward and through the skin to provide the locating means to be used in the biopsy operation.

Figure 6:
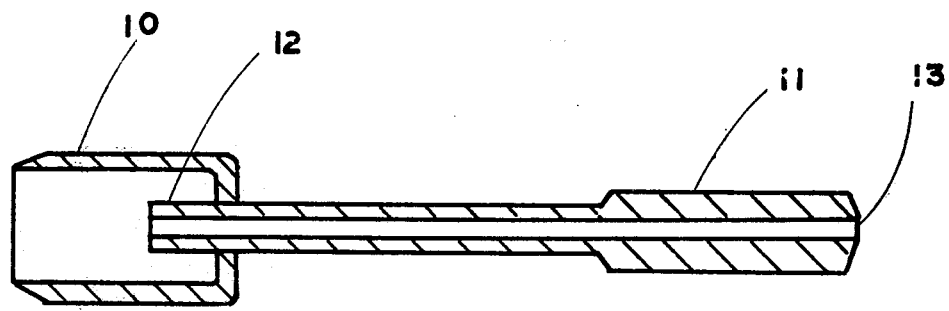
FIG. 6 is a sectional view of a cutting tool.

The method of the biopsy operation is discussed with reference to FIG. 5. When the biopsy is to be performed, the surgeon makes an incision in the skin to provide passage for biopsy tool 9 and thus avoid unnecessary damage to surface tissue. He then slides biopsy tool 9 over wire 4 and applies a light tension to the wire to guide the tool and stabilize the specimen to be cut. Having centered the tool over the target 3 he rotates the tool to cut the sides of the specimen and draw it into the cup of biopsy tool 9. Still maintaining tension on wire 4 he tilts biopsy tool 9 and passes a knife across the bottom of the biopsy tool cup cutting the specimen free. The biopsy tool viewed in FIG. 6 is a cutting means consisting of a cup-shaped cutter 10 with the lip of the cup sharpened, a hollow handle extension 11 knurled on one end to assist in gripping and manipulating the tool, and an extension 12 of the handle tube within the cup to serve as a stop by abutting against the target 3 and to limit the depth of cut. A hole 13 passes through the length of the handle extension to permit the tool to center itself on guide wire 4 attached to target 3 shown in FIG. 5.

Having illustrated and described a preferred embodiment of the invention and having discussed possible variations thereof, it should be apparent to those skilled in the art that changes and modifications can readily be made therein without departing from the spirit and scope of the invention.

We claim as our invention:

1. A method of location and removal of a biopsy specimen comprising:

locating evidence of early cancer by radiography techniques, positioning and implanting an x-ray opaque target in the suspect area as the patient is subject to x-ray examination, extending a locating means from said target outwardly to and through the skin surface, mounting and guiding a cutting means on said locating means, rotating said cutting means to cut a biopsy specimen, and cutting and detaching the bottom of said specimen with a knife.

2. The method of claim 1 wherein said target and surrounding tissue are pulled into said cutting means by applying force to said locating means while rotating said cutting means until said target abuts a stop within said cutting means.

* * * * *